United States Patent [19]
Orlowski

[11] 4,172,323
[45] Oct. 30, 1979

[54] DENTAL PROCEDURES USING ADHESIVE FORMULATIONS

[75] Inventor: Jan A. Orlowski, Altadena, Calif.

[73] Assignee: Lee Pharmaceuticals

[21] Appl. No.: 794,544

[22] Filed: May 6, 1977

[51] Int. Cl.² ............................................. A61C 13/30
[52] U.S. Cl. .................................................... 32/6
[58] Field of Search ................. 32/6, 5, 2, 10 R, 12, 32/15; 264/16, 261

[56] References Cited

U.S. PATENT DOCUMENTS

| 769,631 | 9/1904 | Priest | 32/10 R |
|---|---|---|---|
| 986,653 | 3/1911 | Supplee | 32/12 |
| 1,296,009 | 3/1919 | Richards | 32/10 R |
| 2,826,814 | 3/1958 | Sappey et al. | 32/5 |
| 3,066,112 | 11/1962 | Bowen | 260/42.15 |
| 3,179,623 | 4/1965 | Bowen | 260/837 R |
| 3,194,783 | 7/1965 | Bowen | 260/837 R |
| 3,250,002 | 5/1966 | Collito | 32/6 |
| 3,250,003 | 5/1966 | Collito | 32/6 |
| 3,831,281 | 8/1964 | Edelman | 32/10 R |
| 3,895,445 | 7/1975 | Silverman et al. | 32/14 R |

FOREIGN PATENT DOCUMENTS

| 480399 | 4/1953 | Italy | 32/5 |
|---|---|---|---|
| 500409 | 2/1939 | United Kingdom | 32/5 |

Primary Examiner—Russell R. Kinsey
Assistant Examiner—John J. Wilson
Attorney, Agent, or Firm—Irons and Sears

[57] ABSTRACT

The adhesive bonding of a pontic tooth to the two adjacent, natural abutment teeth is improved, particularly in resistance to shearing forces, by an improved adhesive bonding system. In this system, adhesive is applied to the previously prepared surfaces of the abutment teeth, and a thin screen or perforated film or foil is embedded in the adhesive on each tooth surface, conformed to the shape of the prepared surface, and penetrated by the adhesive. In one preferred embodiment, the adhesive wets and penetrates the surface of the artificial pontic that is being secured in place, the previously prepared abutment tooth surfaces, and the screens or films or foils, so that upon curing, an integral mass results that is mechanically strong, particularly in resistance to shear. The system is useful with natural or artificial teeth, can be used to install fixed bridges, and is useful for splinting.

8 Claims, 6 Drawing Figures

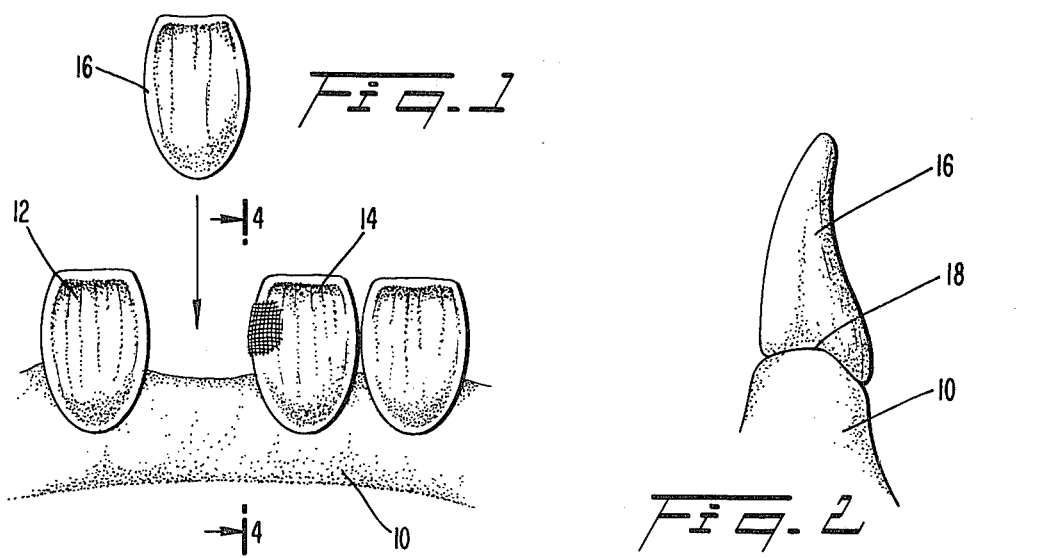
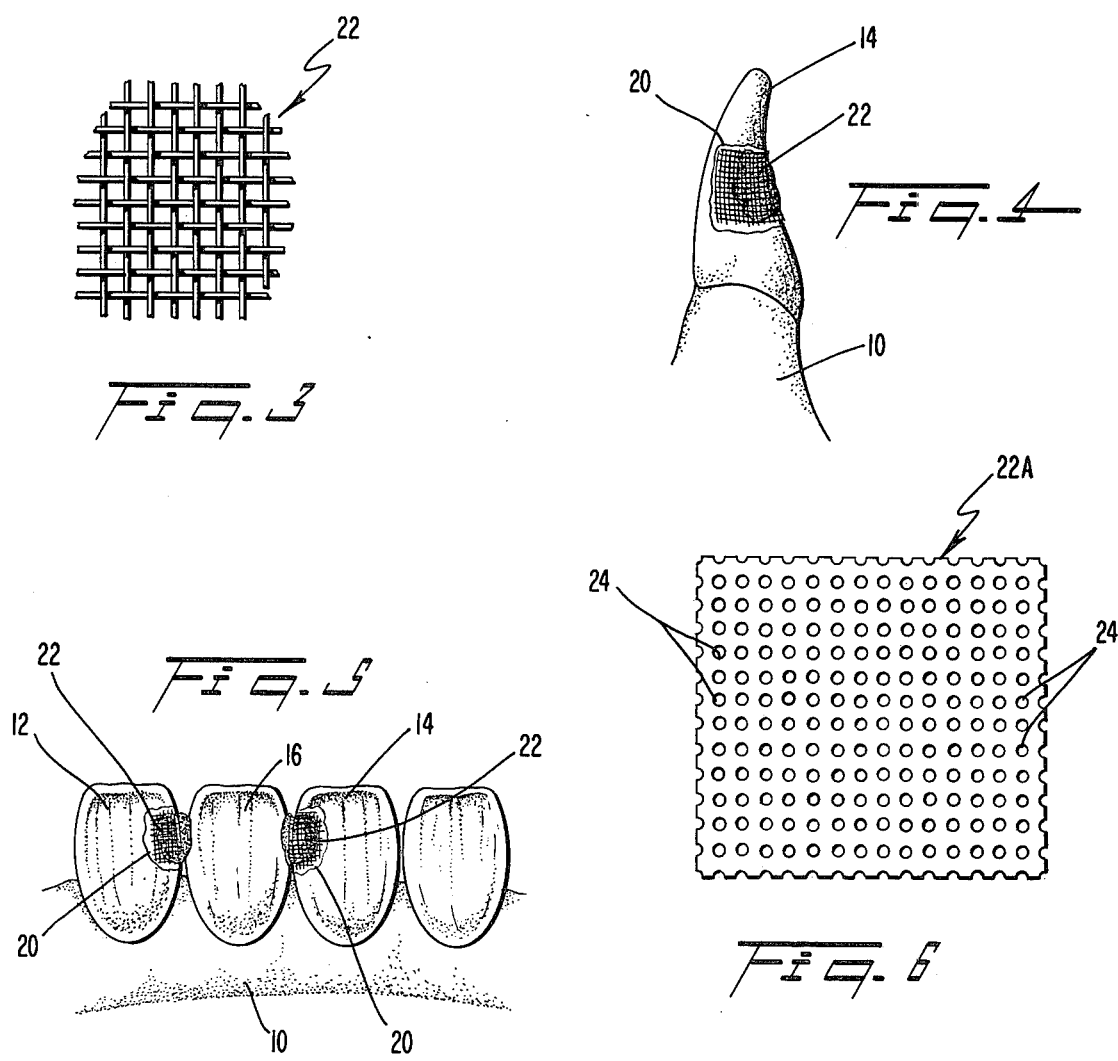

DENTAL PROCEDURES USING ADHESIVE FORMULATIONS

FIELD OF THE INVENTION

This invention is concerned with a method for securing a pontic tooth or fixed bridge in place in the mouth. More particularly, the invention is concerned with a method for securing a pontic or fixed bridge in place on the supporting surfaces of the natural abutment teeth. The invention is also concerned with the resulting structures, and with systems that are useful in carrying out the invention.

DESCRIPTION OF THE PRIOR ART

In the last few years, a technique has been introduced to dentistry for replacing a missing tooth with a fixed bridge consisting of a pontic tooth (either a denture tooth or the patient's own natural crown), or even more than one such tooth, bonded with acrylic adhesive to the two adjacent, natural abutment teeth. The pontic tooth may just rest on the gum, or in the technique known as "splinting," the patient's own extracted tooth is replaced and is set in the gum. Such replacements offer great advantages in speed of installation and convenience, in improved appearance, and in lower cost, over muco-adhesion partials and other appliances. Unfortunately, the experience that has been gained with fixed bridges of this type has not been completely satisfactory. The forces generated during chewing induce adhesive failure, so that such bridges have very short lives, and do not stay in place long. These forces are complicated, and include components of shearing force, compressive force, and rotary grinding force, all of which assault the adhesive bond.

In what may be an oversimplified analysis, it can be postulated that these several forces, that are generated during mastication, are translated into shear forces at the glue line between the pontic, the adhesive, and each abutment tooth. The normal force imposed on any one tooth, by biting on a hard object, is rarely in excess of 100 pounds: *Theory and Practice of Crown and Bridge Prosthesis,* by Stanley D. Tylman, C. V. Mosby Co., St. Louis, 1954, page 175. A load of this magnitude would thus set up a shear load of about 50 pounds at the glue line. The commercially available acrylic-epoxy adhesives have a shear strength on the order of about 2,000 pounds per square inch, when adhered to previously prepared tooth enamel. Thus, the strength of the adhesive bond is governed, if such a theoretical analysis is applied, by the total area of the adhesive contact between the pontic and the support surfaces to which it is bonded.

Assuming that the contact area and contour of the adhesive resemble those of a soldered bridge, a working area of about 0.035 square inches is provided. This area is capable of carrying a shear force load of about 70 pounds. Thus, a bridge of the kind described is capable of carrying normal shearing force loads, but not the abnormal shearing force load imposed on any one tooth by biting a hard object, nor abnormal shearing force loads placed on individual teeth. Moreover, in fact, the forces generated by chewing result in a kind of combined direct shear-compressive-rotary grinding force that is not really susceptible to simple analysis, and forces other than shearing forces undoubtedly have played a role in adhesive failures.

Although prior workers have concerned themselves with the problems of dental adhesives, none have faced or solved the problem of developing an adhesive bond that could withstand chewing forces in a dental environment over a period of time that would permit a bridge installation to be regarded as permanent. Thus, in U.S. Pat. Nos. 3,250,003 and 3,895,445, the patentees were concerned with the problem of securing orthodontic brackets and other appliances to the teeth. In this kind of an application, the adhesive is not subjected to chewing forces, and the only conditions of use that are analogous are those environmental factors that exist because of location in the oral cavity. In U.S. Pat. No. 3,250,003, the patentee recognized that adhesive bonds within the oral cavity are subject to attack by moisture and chemical action, and that the tenaciousness of the bond over protracted periods may be improved by the use of a sealing agent that isolates the adhesive from the oral environment. The approach taken was to use a cyano-acrylic bracket adhesive, protected by an epoxy resin sealing material. In U.S. Pat. No. 3,895,445, an orthodontic bracket was seured to a tooth through the use of two layers. The first layer, that was bonded to the tooth, was a thermosetting sealing composition containing the reaction product of bisphenol A and an epoxy ester of methacrylic acid. The bracket was secured to this layer of thermosetting sealer composition on the tooth by a thermoplastic bonding composition. One preferred formulation for the thermoplastic bonding composition was a blend of polymethyl methacrylate and polycyclohexyl methacrylate in liquid hexyl methacrylate. Neither patentee had to face the problem of providing resistance to chewing forces.

Experience with adhesively secured fixed bridges and with adhesively secured orthodontic brackets indicates that failure at the adhesive bond, when it occurs, seems to be due to the application of chewing forces that cause adhesive failure. The failure may occur because of brittleness. This would tend to lead one in the direction of increasing the resilience of the adhesive bond, but that is not the direction followed by the present invention.

SUMMARY OF THE INVENTION

In one aspect, the present invention is a method for securing a pontic tooth or fixed bridge in place on the support surfaces of abutment teeth in the mouth. More particularly, the present invention is concerned with securing a pontic tooth, either natural or artificial, in place on previously prepared supporting surfaces on the adjacent, natural abutment teeth in the mouth.

The invention involves applying to the previously prepared support surfaces of the abutment teeth a liquid dental adhesive that wets the surfaces, to insure good bonding. A screen is then applied to each support surface. The screen may be a molded polycarbonate screen, or a film or foil that is formed with a series of evenly spaced small holes. It must be made from a material that conforms readily to the shape of the support surface, so that in must have a high degree of flexibility and be free from plastic memory or resilience. Adhesive is then applied between the pontic or fixed bridge and the screen, and the pontic or bridge is then held in its desired final position while the adhesive cures, which should not be in excess of 10 minutes. The curing process forms a strong adhesive bond, with the screen embedded in the adhesive.

The resulting adhesive bond has been found to be mechanically strong, particularly with respect to resistance to shearing forces. While not wishing to be bound by any theory, it appears likely that the screen prevents the application of any high shear force in a very localized area, and distributes it over the entire adhered area. For whatever reason, adhesively fixed bridges produced in accordance with the present invention have been installed and in use on an experimental basis without any observed failure in the adhesive bond.

In one preferred embodiment of the invention, the prepared tooth surfaces, the screen, and the artificial pontic used all are penetrated by the adhesive, so that upon curing, an integral mass is formed that has unusual mechanical strength.

BRIEF DESCRIPTION OF THE DRAWING

In the drawing:

FIG. 1 is a fragmentary view, in elevation, of a human lower jaw (seen from the inside) from which one tooth, such as a lateral incisor, is missing, with a pontic shown above the vacant space, the pontic being of a shape and size suitable for installation as a part of a fixed bridge;

FIG. 2 is a fragmentary side elevation view of an artificial pontic seated on the gum, to replace a missing tooth, showing how the pontic can be shaped to seat lightly on the gum;

FIG. 3 is a plan view, on an enlarged scale, of a screen for use in accordance with the present invention;

FIG. 4 is a fragmentary side elevation, taken on the line 4—3 of FIG. 1, looking in the direction of the arrows, showing a screen placed in a layer of adhesive on the prepared surface of an abutment tooth, for use in making a fixed bridge installation in accordance with this invention;

FIG. 5 is a fragmentary elevation of the human lower jaw shown in FIG. 1, again from the lingual side, with the pontic adhesively secured in place in accordance with one embodiment of this invention, and showing the projecting ends of the screens that are embedded in the adhesive on the supporting surfaces of the abutment teeth, and FIG. 6 is a plan view, on an enlarged scale, of a perforated plastic film that can be used in place of the screen in accordance with another embodiment of the invention.

DETAILED DESCRIPTION OF THE INVENTION

While the invention is illustrated in the drawing by application to the securing of a pontic in place to form a fixed bridge, the invention is equally applicable to securing larger items in place, such as, for example, a bridge made of two artificial pontics molded together or, alternatively, bonded together in accordance with the present invention, and the invention is equally applicable to splinting, where the pontic is set in the gum. One caveat is that the support surfaces in the mouth, to which the adhesive bond is to be made, must be free of gold or amalgam restorations, that is, suitable surfaces must be available for bonding.

To make a fixed bridge from a single pontic, in accordance with the present invention, the following general technique can be followed, with reference to the drawing by numerals of reference.

First, an impression is taken of the jaw from which the tooth is missing, and a pontic is obtained. The pontic is shaped to fit the model. The impression would be taken of the lower jaw 10 and would show the two natural abutment teeth 12 and 14, having a vacant space between them. The pontic 16 would be shaped to fit this vacancy and its size would be such as to permit minimal clearance with the confronting surfaces of the natural abutment teeth 12 and 14. The lower face 18 of the pontic would be shaped as shown in FIG. 2, to rest lightly on the gum of the lower jaw 10.

When the fixed bridge is to be installed, an optional step may be taken to improve the mechanical bond. In many cases, this optional step is not necessary, particularly where only a single pontic bridge is to be installed, and therefore this step is not shown in the drawing. This optional step consists of making mechanical undercuts or grooves in the pontic to assist in retention and further resist shear forces. The preferred form for these optional undercuts and grooves is achieved by cutting a series of lingual grooves from mesial to distal with a coarse fissure burr across the lingual surface. One or two coarse undercuts may be made on each promimal surface of the pontic. Any roughened material should be left in place, further to assist in retention, but any loose material should be dressed away. The surfaces of the grooves should be left as coarse as possible.

Next, the contact areas of the proximal surfaces of the abutment teeth are dressed with a coarse diamond or a coarse garnet, so as to remove plaque, cuticle, protein, weak enamel, and the like. Optionally, small undercuts in the enamel may be made in the contact area, also for the purpose of increasing the area available for bonding and the resistance to shear forces.

The bridge area is then isolated with cotton rolls, and a mild etching agent is applied to the support surface areas of the abutment teeth. Suitable etching agents are well known and include solutions of phosphoric acid and citric acid, for example. After two to three minutes, the etching agent is rinsed off with water and dried.

After etching, washing, and drying, a dry field is maintained, either by air or by the use of a dental drying agent such as, for example, a mixture of equal parts of acetone and diethyl ether, or one of the other drying solutions disclosed in the copending U.S. patent application of Henry L. Lee, Jr. and Jan A. Orlowski, Ser. No. 588,507, filed June 19, 1975, or in its parent application, now U.S. Pat. No. 3,905,110. The appropriate surface areas of the pontic are also kept dry. Removal of all moisture is desirable since it has a deleterious effect upon many dental adhesives, such as those that are preferred for use in the present invention.

Once the bonding surfaces of the abutment teeth and of the pontic have been etched, washed, and dried, they should not be touched with either fingers or instruments. Similarly, the patient should not be permitted to cause the treated areas to become moist with saliva, since this could cause the adhesive bond to be inadequate.

At this point, a layer 20 of the adhesive is applied on each support surface of the abutment teeth. The adhesive should be applied as thin liquid that readily wets the surfaces of the teeth. Next, the adhesive is applied as a thin coating to each side of the two screens 22 that are to be used, and one screen 22 is applied to each abutment tooth surface. The screen 22 should be positioned so that it is not visible from the front, but it should be sufficiently large to cover the entire area of each abutment tooth that will be engaged by the pontic, and it may extend a short distance around to the back or lingual surface of each abutment tooth, as shown in FIG. 5. Adhesive is then applied to the pontic, and the pontic is then placed in position and held without stress until initial set occurs, which should take place within two to three minutes. In applying the adhesive, if grooves and undercuts have been employed, they should be completely filled with the adhesive.

Once initial set has occurred, additional adhesive can be added, to increase the area of the bond, although usually added adhesive is not necessary. The adhesive should be permitted to cure for at least twenty to thirty minutes, before any stress is applied to the pontic. At the end of a resonable cure time without the application of stress, the excess adhesive can be removed to establish proper embrasures and to produce the desired cosmetic appearance.

The term "screen" is employed in this application in a generic way, to refer to a plastic screen or to a perforated plastic or metal sheet, foil or film of flexible material having limited resiliency. The screen or film should be flexible and formable, and lacking in plastic memory, so that it can conform readily and permanently to the contour of the abutment tooth on which it is placed. Polycarbonate and acrylic plastics are most useful for this purpose, but several types of nylon, polyester, polyacrylonitrile, and some vinyl polymers, that are suitable for use in the oral cavity, may be used. Alternatively, a thin perforated metal foil or metal screen may be utilized. The thickness of the screen or foil should be in the range from about 0.1 mm. to about 1.0 mm. and preferably in the range from about 0.1 mm. to about 0.5 mm. The size of the screen that is used should be sufficient so that the confronting, engaged surface areas of the pontic and of the two abutment teeth are covered when the screen is applied. The openings or perforations in the screen should constitute a substantial portion of its area, generally about 50%, or even more.

The adhesive may be any suitable high bonding strength dental adhesive, including many of the formulations used in dental composite restoratives, one qualification upon this being that any inorganic filler present should be limited in quantity to not more than 60% by weight of the adhesive composition and preferably less. Indeed, it is contemplated that no fillers may be used, or that particulate precured polymers may be employed pontic to a depth of a millimeter or more. While the adhesive composition need not contain any filler, in preferred embodiments of the invention, precured polymeric particles are employed as the filler and are also penetrable by the liquid binder, so that the filler particles also become part of the integral mass upon curing.

The screen is formed from an open mesh of filaments that are bonded together where they intersect and engage each other, to form a fixed but flexible structure. Even more preferably, the screen is made from a film of a plastic material that is formed with a series of equally sized, uniformly spaced holes 24 (FIG. 6). The screen is readily conformable to the shape of a supporting surface on which it is placed, but after it has been embedded in adhesive and the adhesive has been cured, the screen should remain rigid and immovable. This results in a product with superior resistance to shear forces and with otherwise good mechanical properties.

The thickness of the screen serves to control the spacing between the pontic and the support surface of each abutment tooth. One cause of previous failures of prior art adhesively secured fixed bridges may have been too great a reliance on a thick adhesive joint, and the use of a thick joint in itself may have led to the type of failure that is consequent from a brittle joint.

The preferred adhesive composition is one in which the resin binder contains as at least 30% by weight of the binder, and preferably as about 50% to 60% by weight of the binder, but as not more than about 80% by weight of the binder, an acrylic ester that contains an epoxy group, preferably glycidyl methacrylate, the balance being a crosslinking agent. The epoxy ester of acrylic acid or methacrylic acid can be generally described as an ester of methacrylic acid or acrylic acid with a monoalcohol that contains at least one epoxy group. While glycidyl methacrylate is the preferred component, other satisfactory materials that can be used either alone or in admixture with other similar materials include glycidoxyl propyl methacrylate, and the esters that are obtained by reacting a variety of different epoxy compounds with acrylic acid or methacrylic acid to produce monomers having at least one epoxy group, of which the following formula is exemplary:

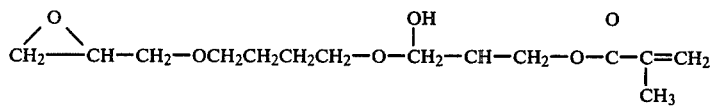

that are sufficiently compatable with the liquid binder of the adhesive so that upon cure a monolithic or integral mass is obtained. In any case, the adhesive that is selected must readily wet the surfaces of the pontic and of the abutment teeth, and the screen as well, to be suitable.

DETAILED DESCRIPTION OF A PREFERRED EMBODIMENT

In a preferred embodiment of the invention, the adhesive composition has a liquid binder that not only readily wets the surfaces of the pontic and of the abutment teeth, and also has the ability to penetrate into the etched tooth surfaces, into the pontic, and the screen as well. The end product of this preferred embodiment is a bond wherein the adhesive is cured not only on the surfaces of the abutment teeth but also where it penetrates into these surfaces in "tags" that may be many microns long, and that may penetrate a compatible Preferred cross-linking agents include, for example, diethylene glycol dimethacrylate, triethylene glycol dimethacrylate, bis(methacroyl-2-hydroxy-propoxy)-bisphenol A(bis/GMA), and bis(methacroyl-ethoxy) bisphenol A(EBA).

Thus, the liquid component of the resin binder of the adhesive is no less than 30%, and preferably is 50%-60% by weight, but not more than 80% by weight, of glycidyl methacrylate, together with one or more of an optional, compatible, copolymerizable acrylic ester monomer, preferably one that contains an epoxy group, and at least 20%, and preferably 40%-50%, of a cross-linking agent that is a di-, tri-, or poly- acrylate or methacrylate. The adhesive must be sufficiently fluid, that is, low enough in viscosity, so that the tooth and pontic surfaces are readily wetted.

The adhesive composition may contain no filler whatever, or may contain up to 60% by weight of the composition of a particulate filler. When a filler is employed, it is preferred that the filler be in the form of finely divided, precured particles of a polymer that is at least partially soluble in the monomeric portion of the resin binder.

The adhesive may be formulated and packaged in any conventional or convenient way. Thus, it may be packaged in two portions in the usual fashion, as a gel/liquid, paste/paste, powder/liquid, or paste/liquid. The precise form of packaging is not important, so long as the adhesive composition, as made up for use, readily wets the surfaces to which it is applied, for optimum bond development.

The pontic may be either an acrylic artificial pontic, or a pontic made of some other satisfactory polymeric material, preferably one that is at least partially soluble in the liquid binder of the adhesive composition, or it may be the patient's natural tooth or crown. When a natural tooth is used, it may be set in the gum, in the known fashion for splinting. When the patient's crown is used, the roots are cut off and the crown is dressed to the desired dimensions. The roots are cleansed and obturated by injecting a suitable adhesive. The crown can then be treated in the same way that an artificial pontic would be treated.

The invention will now be illustrated further by reference to specific examples. All parts and percentages herein are by weight unless expressly stated to be otherwise.

EXAMPLE 1

An acrylic pontic is selected from a supply of commercially available plastic teeth, for use in making a bridge to replace a missing tooth. The plastic pontic is cut and dressed to fit the patient's mouth.

The screen used is a polycarbonate film about 0.2 mm. thick, and formed with a series of small, uniformly spaced, equally sized holes that occupy more than ½ of its surface area.

The adhesive employed has the following formula:

| Component | Parts by Weight |
|---|---|
| Glycidyl methacrylate | 34 |
| Bis (methacroyl-2-hydroxy-propoxy) bisphenol A | 24 |
| Copolymer of ethyl and methyl (50/50) methacrylate (powder) | 19 |
| Silica powder (10-20 microns) | 19 |
| Benzoyl peroxide | 2.9 |
| N,N-bis(hydroxyethyl)-p-toluidine | 1 |
| Titanium dioxide | 0.1 |

The appropriate surface areas of the abutment teeth are etched for about two minutes with a 50% solution of phosphoric acid. After rinsing and then drying with air, these surfaces and the surfaces of the pontic are treated with a drying agent made from equal parts of acetone and diethyl ether, and are permitted to dry. The support surface areas of the abutment teeth are then coated with the adhesive, both sides of the two screens are coated with adhesive, and each screen is placed on the support area of one of the abutment teeth, respectively. Each screen is carefully conformed to the shape of its abutment tooth. Each screen is positioned so that, while it covers substantially the entire proximal surface area that will confront and engage against the pontic, no part of the screen projects around the front or labial tooth surface, so that the screen is not visible from the front. A small part of the screen extends around to the rear or lingual surface of the tooth. A coat of adhesive is then applied to each of the side surfaces of the pontic, and the pontic is then properly positioned and held in place for about two minutes until an initial set occurs. A small amount of additional adhesive is then applied to eliminate crevices. After curing, the bridge is dressed.

Such a fixed bridge gives excellent service.

ADDITIONAL EXAMPLES

Other bridges can be installed using different adhesive formulations and different screens, but following generally the procedure outlined above. In each case an acrylic tooth is used, and the liquid component of the adhesive formulation is sufficiently compatible with the artificial pontic material to penetrate partly into the pontic for curing.

Table 1

| Component | Parts by Weight Example No. | | |
|---|---|---|---|
| | 2 | 3 | 4 |
| Glycidyl methacrylate | 25 | 25 | 34 |
| Diethylene glycol dimethacrylate | 25 | — | — |
| Copolymer of ethyl and methyl (50/50) methacrylate (powder) | 46 | 46 | 19 |
| N,N-bis (hydroxyethyl)-p-toluidine | 1 | 1 | 1 |
| Titanium dioxide | 0.1 | 0.1 | 0.1 |
| Benzoyl peroxide | 2.9 | 2.9 | 2.9 |
| Triethylene glycol dimethacrylate | — | 25 | — |
| Bis(methacroyl-ethoxy) bisphenol A | — | — | 24 |
| Silica powder (10-20 microns) | — | — | 19 |

The screen that is preferred for use with the adhesive compositions of Table 1 is a polycarbonate film about 0.2 mm. thick, perforated with a series of uniformly sized evenly spaced small holes that preempt about 50% of the surface area of the film. Each of these can be used to form a satisfactory fixed bridge with an acrylic artificial pontic, that is highly resistant to shear forces.

CONCLUSION

The liquid binder portion of the adhesive that is employed preferably is one that is cured with peroxide catalysts but could as well be one that is cured by ultraviolet light under properly controlled conditions. For convenience in use, the adhesive should be one that cures in not less than one minute, and preferably not less than about two minutes, and in not more than ten minutes.

In making a fixed bridge, the preferred pontic for use is one formed of an acrylic plastic. However, a pontic formed of porcelain or a natural tooth may also be employed. In addition, a composite restorative molded tooth, or a tooth made from any suitable substrate having an acrylic or porcelain veneer or facing, may be employed. Preferably, the pontic is either an acrylic plastic tooth or a tooth that is faced or veneered with acrylic plastic.

While the invention has been disclosed by reference to the details of preferred embodiments thereof, it is to be understood that such disclosure is intended in an illustrative, rather than in a limiting sense, and it is contemplated that various modifications in the construction of the screen and in the formulation of the adhesive, in particular, will readily occur to those skilled in the art, within the spirit of the invention and the scope of the appended claims.

What is claimed is:

1. An improved method for adhesively mounting in the mouth a dental article that is a pontic or a fixed bridge of one or more pontic teeth, in such fashion as to withstand the forces generated on the teeth as by chewing, by securing bonding surfaces on the article to be mounted in the mouth to previously prepared support surfaces respectively of abutment teeth that are adjacent the mounting location for the article but at opposite sides of it respectively, comprising:

applying to each of the prepared support surfaces a flowable dental adhesive and a screen having a thickness up to about 1.0 mm., that conforms readily to the contours of the support surface of the respective abutment tooth to which it is applied, and conforming the screen to said contours;

positioning the article with each of its respective bonding surfaces in a desired position relative to the adjacent, abutment teeth and their respective screen-covered confronting support surfaces, for permanent installation of the article in that position, and interposing adhesive between each said bonding surface on the article and the screen it confronts, and each said bonding surface on the article and the screen in confronts, and permitting the adhesive to harden to bond the dental article in place with a screen interposed between each of its bonding surfaces and the respective confronting support surface and embedded in the adhesive, and forming with the adhesive a mechanically strong bond.

2. A method in accordance with claim 1 wherein the dental adhesive comprises a resin binder that penetrates into the prepared support surfaces of the abutment teeth, and each screen is formed from a synthetic resin, and wherein the solid portions of the screen are penetrated by the adhesive before it hardens, so that upon hardening of the adhesive the screen is integrally bonded to the adhesive as well as embedded in it.

3. A method in accordance with claim 2 wherein the screen is a flat foil or film that is formed with spaced small holes through which the adhesive flows upon application to the screen, to fill the holes.

4. A method in accordance with claim 2 wherein each screen is a molded screen having fine intersecting filaments of a polycarbonate resin and an evenly space series of small holes through which the adhesive can flow.

5. A method according to any of claim 1 wherein the dental adhesive comprises a resin binder of which from 30% to 80% by weight of the binder is an ester of methacrylic acid with a monoalcohol containing at least one epoxy group, and the balance of the binder is a cross-linking agent selected from the group consisting of aliphatic dimethacrylates and aromatic dimethacrylates.

6. An improved method for adhesively mounting a pontic in the mouth, in such fashion as to withstand the forces generated by chewing, by securing bonding surfaces on the pontic to previously prepared support surfaces respectively on abutment teeth that are adjacent the mounting location for the pontic but at opposite sides of it respectively, comprising:

applying to each of the prepared support surfaces a flowable dental ahesive and a screen having a thickness in the range from about 0.1 mm. to about 1.0 mm., which screen conforms readily to the contours of the support surface of the respective abutment tooth to which it is applied, and which adhesive has a liquid binder containing from about 50% to about 60% by weight of the resin binder of glycidyl methacrylate, and from about 40% to about 50% by weight of the resin binder of a dimethacrylate cross-linking agent, in combination with no more than about 5% by weight of a polymerization catalyst and an accelerator, and conforming the screen to said contours;

positioning the pontic with each of its respective bonding surfaces in the desired location relative to the adjacent abutment teeth and their respective screen-covered confronting support surfaces for permanent installation of the pontic in that location, and interposing adhesive between each bonding surface and the confronting screen, and permitting the adhesive to harden to bond the pontic in place with a screen interposed between each of its bonding surfaces and the respective confronting support surface and embedded in the adhesive, and forming with the adhesive a mechanically strong bond.

7. A method in accordance with claim 6 wherein the pontic is formed from an acrylic resin and wherein the resin binder of the adhesive penetrates the surfaces of the pontic and also projects into the ethced support surfaces of the abutment teeth.

8. A method in accordance with claim 7 wherein the screen is molded from a polycarbonate resin and the adhesive penetrates into the solid part of the screen and fills its holes.

* * * * *